(12) United States Patent
Rom (10) Patent No.: US 11,701,305 B2
(45) Date of Patent: Jul. 18, 2023

(54) UNIT DOSE SACHET COMPRISING A PERFUME GEL COMPOSITION

(71) Applicant: Spritz, Inc., Wilmington, DE (US)

(72) Inventor: Tom Rom, Los Angeles, CA (US)

(73) Assignee: SPRITZ, INC., Wilmington, DE (US)

( * ) Notice: Subject to any disclaimer, the term of this patent is extended or adjusted under 35 U.S.C. 154(b) by 84 days.

(21) Appl. No.: 17/347,884

(22) Filed: Jun. 15, 2021

(65) Prior Publication Data
US 2022/0395434 A1   Dec. 15, 2022

(51) Int. Cl.
| | |
|---|---|
| *A61K 8/02* | (2006.01) |
| *A61K 8/11* | (2006.01) |
| *A61K 8/81* | (2006.01) |
| *A61K 8/04* | (2006.01) |
| *A61Q 13/00* | (2006.01) |
| *C11B 9/00* | (2006.01) |
| *A61K 8/92* | (2006.01) |

(52) U.S. Cl.
CPC ............ *A61K 8/0208* (2013.01); *A61K 8/042* (2013.01); *A61K 8/11* (2013.01); *A61K 8/8147* (2013.01); *A61K 8/922* (2013.01); *A61Q 13/00* (2013.01); *C11B 9/00* (2013.01); *A61K 2800/48* (2013.01); *A61K 2800/49* (2013.01); *A61K 2800/52* (2013.01)

(58) Field of Classification Search
None
See application file for complete search history.

(56) References Cited

U.S. PATENT DOCUMENTS 5,985,821 A    11/1999   Dobler et al.

FOREIGN PATENT DOCUMENTS

| JP | H 03272766 A | 6/1999 |
| JP | 2007-261998 A | 10/2007 |
| JP | 2011-055884 A | 3/2011 |
| KR | 101673474 B1 | 11/2016 |
| KR | 2021-0047069 A | 4/2021 |

OTHER PUBLICATIONS

Gregolin et al., "Rheological Characterization of Hydrophylic Gels" Journal of Dispersion Science and Technology, vol. 31, 2010—Issue 6pp. 820-825, May 13, 2010.

(Continued)

*Primary Examiner* — Arrie L Reuther
(74) *Attorney, Agent, or Firm* — Knobbe, Martens, Olson & Bear, LLP (57) ABSTRACT

The invention relates to a unit dose sachet comprising a perfume composition, wherein the perfume composition is a gel which comprises i) 0.2 to 2.0% by weight of a gelling agent selected from acrylates/$C_{10}$-$C_{30}$ alkyl acrylate cross polymers; ii) 60.0 to 75.0% by weight of a cosmetically acceptable alcohol; iii) 0.8 to 9.0% by weight of a fragrance composition having a liquid bulk specific gravity 20/20° C. of 0.97 to 1.08, a refractive index at 20° C. of 1.45 to 1.53 and a flash point of 100° C. to 1000° C.; iv) 0.5 to 1.5% by weight of a stabilizer; and v) 0.5 to 2.4% by weight of a solubilizer, vi) water up to 100% by weight, wherein the composition has a viscosity of 17,500 to 24,200 cps, and wherein the ratio of fragrance composition:gelling agent: alcohol is from 1:0.06:6 to 1:0.16:12.5.

10 Claims, 3 Drawing Sheets

(56) References Cited

OTHER PUBLICATIONS

Shalaby et al., "The Influence of the Type and Concentration of Alcohol on the Rheological and Mucoadhesive Properties of Carpobol 940 Hydroalcoholic Gels" Der Pharmacia Sinica, 2011, 2(6):161-171.

Tzaneva et al., "Rheological Properties of the Cosmetic Gel Including Carboxymethyl Chitosan" J. Pharm. Sci. & Research, vol. 9(8), 2017, 1383-1387.

Nichol, Katie. "How beauty sampling is adapting to post-covid retail." Luxe Publishing Insight, published Jun. 4, 2020.

UNIT DOSE SACHET COMPRISING A PERFUME GEL COMPOSITION

BACKGROUND OF THE INVENTION

Field of the Invention

The present invention relates to a unit dose sachet com-prising a perfume com-position for personal use in a liquid-like gel form with a specific viscosity and with specific rheological characteristics packed in disposable unit dose sachets. The sachets are designed for a once a time use and are comprised in packages containing a minimum of 30 sachets, i.e. a monthly ration of said perfume sachets. Said perfume sachets are intended to be sold under the brand name Spr1tz.

Description of the Related Art

The classical image of perfumery products always entails the perfume bottle. Over centuries a high quality glass bottle has been associated with a perfumed product. Such per-fumed bottles usually are associated with high production costs and a high resource consumption and create a lot of waste. There is a need for a fragrance product that addresses the $21^{st}$ century need for a protective product that preserves the person who uses it indoors and outdoors or in other spaces from contamination and at the same time reserves the ability of the user to enjoy the pleasant experience of personal perfuming using a middle weight product with ecological features to take part of preserving the environment from unnecessary glass bottles and industrial waste.

A 2019 article written for the Bosch Company by Frank Buhler, "How convenience and the on-the-go culture drive packaging miniaturization across the globe" examines the tremendous potential of individual sachet packs in the millennial trading market.

The article argues that in developed countries, there is a growing need for customers in products that will make fast-paced life outside the home space easier.

The population that most prominently reflects this idea is Generation Y, also known as the Millennium Ball (born 1980-2000), who tend to consume products characterized by ease and time savings. The Million Generation is the largest and most lucrative age group in the market, with technology and individual choice being key elements in their consumption patterns.

The millennial generation is also creating a significant demographic change, as more and more single-person households are emerging in urban spaces. Therefore, the need for large packages (also called "family packages") is diminishing.

The trend of mini packaging is also developing due to the individualistic consumption of the younger generation. Consumers tend to define themselves according to the products they consume, and according to the way they are perceived and experienced by others according to their consumption. Therefore, consumers tend to test a wide range of products and brands in order to find the perfect fit according to their personal taste, which makes them visit stores more frequently, in order to choose the product that suits them at that moment.

Toiletries like shampoo, shower gel and body lotion packaged in bag packs have become extremely popular for outdoor living. The personal care market grew from 9.4 billion individual packaging units in 2012, to 22.6 billion individual pack-aging units in 2017, a tremendous development that is estimated to grow by 19.3% per year.

The research shows a growing need in both popular culture and academia to find new and alternative ways to produce perfume packages, especially considering the growing need to reduce the use of pollutants such as plastic and glass. An example of this emerges from a thesis written in the Department of Design at the University of Lahti, Finland in 2016 "Future perspective: Design process of per-fume packaging" published by Lahti University of Applied Sciences Institute of Design and Fine Arts Degree Programme in Design Packaging Design and Branding Duncan K. Anderson Final Thesis Autumn 2016. The thesis writer examined possible scenarios related to resources, infrastructure and consumer behavior in about thirty years, in 2050. The author created a perfume package influenced by his research in 3D printing and other ecological technologies.

In April 2019 the National Geographic Research Organization published the article "The beauty industry generates a lot of plastic waste. Can it change?" Writ-ten by Alejandra Borunda. This reveals that the cosmetics industry produces huge amounts of plastics that pollute the environment, and examines how this phenomenon evolved, and whether it can be eradicated.

The global personal care industry, valued at about $500 billion a year, is mostly based on plastics.

Despite the growing awareness of the importance of plastic recycling, there are types of plastics that cannot be fully or partially recycled.

There are manufacturers for whom the cost of using plastic is too high, and therefore more and more manufacturers are trying to reconsider how their own products are manufactured, their packaging, and their supply chain.

In the not-so-distant past, personal care products did not include plastic packaging. A perfume, as a symbol of luxury, was made in glass packaging.

The personal care industry adopted the use of plastics in the mid-$20^{th}$ century. The plastic made it possible to design lightweight, flexible and stable packaging, and now, products could be distributed more easily around the world.

In light of these changes, the personal care industry developed and grew: in 1919 it was worth $60 million in the United States, and by 1938 it was already worth $400 million. By the 1970s its value was estimated at billions. The more products were produced, the greater the need for new packaging.

Today, the U.S. personal care industry is worth $90 billion.

At the same time, the plastics industry also grew to enormous proportions. The amount of plastic packaging in the US (in general, not just personal care products) has increased more than 120 times since 1960, when almost 70% of plastic waste is piled in landfills. In general, the packaging industry for personal care and beauty products, which uses mainly plastic, nearly $25 billion in sales.

In light of the significant harm to the environment, there is a growing awareness among consumers and government officials of the need to reduce the use of plastics. Therefore, many cosmetics companies are trying to adapt their products to the new need, such as Unilever and L'Oréal.

U.S. Pat. No. 5,985,821 discloses a spreadable fragrance gel product consisting by weight of 10-20% fragrance oil, 80-85% alcohol, and 5% polymer to increase the viscosity of the oil and alcohol to the point where it will not readily pour from a bottle but maintains spreadable. Said product, however, is not intended as a standalone product but is intended to be a sample or substitute or addition to a branded perfume pack in glass or plastic. Moreover, said product does not have rheological properties to be suitable for use in a unit dose sachet for daily consumption.

There is a need to provide a fragrance product that accommodates to the 21$^{st}$ century lifestyle for personal use products. There is a need for providing everyday perfumery products in a suitable size for indoor and outdoor consumption. The products should allow an easy and time saving use. Moreover, the product should be suitable for daily use, give the consumer the experience of necessity and of personal refreshment during daily life.

SUMMARY OF THE INVENTION

The present invention relates to a unit dose sachet comprising a perfumed composition, wherein the perfumed composition is in a gel form and is intended for final use. The specific composition of the gel and the ratio between the ingredients in the perfume composition enables the gel to have Newtonian characteristic and hence, to ensure the constant experience of the user with a stable viscosity parameter of the gel perfume. The stable viscosity is enhanced by the specific composition of all ingredients.

The invention relates to a unit dose sachet comprising a perfume composition, wherein the perfume composition is a gel which comprises i) 0.2 to 2.0% by weight of a gelling agent selected from acrylates/$C_{10}$-$C_{30}$ alkyl acrylate cross polymers; ii) 60.0 to 75.0% by weight of a cosmetically acceptable alcohol; iii) 0.8 to 9.0% by weight of a fragrance composition having a liquid bulk specific gravity 20/20° C. of 0.97 to 1.08, a refractive index at 20° C. of 1.45 to 1.53 and a flash point of 100° C. to 1000° C.; iv) 0.5 to 1.5% by weight of a stabilizer; and v) 0.5 to 2.4% by weight of a solubilizer, vi) water up to 100% by weight, wherein the composition has a viscosity of 17,500 to 24,200 cps, and wherein the ratio of fragrance composition:gelling agent: alcohol is from 1:0.06:6 to 1:0.16:12.5.

The above physical characteristic will basically be determined according to European commission for cosmetic regulations and guidance, for example https://ec.europa.eu/growth/sectors/cosmetics_en and COSMETLEX guidance op.europa.eu/en/publication-detail/-/publication/17655e26-e423-4179-adcc-0bac7d666ebb.

Specific methods for fragrance concentrate described in IFRA guidelines ifrafragrance.org/safe-use/scientific-guidance The specific gravity is the ratio of the density of a substance to the density (mass of the same unit volume) of a reference substance. Usually, the reference substance is water at a particular temperature. The specific gravity is determined according to methods which are standard in the art.

The viscosity of a fluid is the measure of the property of a fluid substance of absorbing a stress during deformation which depends on the rate of the deformation. For Newtonian liquids, the viscosity is constant at all shear rates and depends only on the variables pressure and temperature. For non-Newtonian liquids the viscosity will vary with shear rate. If the viscosity is measures with capillary viscometers without applied pressure, the measured quantity obtained, kinematic viscosity (v), is the ratio of dynamic viscosity to density ($v=\eta/\rho$). The viscosity can be determined according to established methods which are standard in the art.

The refractive index of a substance is the ratio of the velocity of light in air to the velocity of light in the substance. It is valuable in the identification of substances and the detection of impurities. Various specification of the refractive index are known in the art. Usually, the standard temperature for determining the refractive index is 20 or 25° C. The temperature should be carefully adjusted and maintained, since the refractive index varies significantly with temperature. The refractive index is measures by a refractometer, for example by an Abbe refractometer or a digital refractometer.

The flashpoint of a volatile material is the lowest temperature at which it can vaporize to form an ignitable mixture in air. Measuring a flashpoint requires an ignition source. At the flashpoint the vapor may cease to burn when the source of ignition is removed.

The invention, moreover, relates to a package comprising a monthly supply of said unit dose sachet.

Further to this, the invention relates to the cosmetic use of said unit dose sachet for creating a scented atmosphere surrounding a human body by rubbing the composition into the skin.

DETAILED DESCRIPTION OF THE PREFERRED EMBODIMENT

The present invention contemplates the formation of a Newtonian gel perfume/fragrance composition that is suitable for packing in a unit dose sachet and is suitable for everyday use. Hence, there is provided a new and novel way of applying fragrances to a person.

There has been a lot of research on the rheological variety and characteristics of alcohol gels featuring the viscosity, the flow index and the stability of the polymer gel as dominant characteristics of the final gel product in practical use. For example, Samia Shalaby et al., Der Pharmacia Sinica, 2011, 2 (6):161-171 provides a study on the influence of the type and concentration of the alcohol (ethyl alcohol and isopropyl alcohol) on the rheological and mucoadhesive properties of Carbopol 940 gel formulations. It was shown that the type and concentration of the incorporated alcohols significantly affects the rheological and mucoadhesive properties of the prepared Cp 940 gels. It was concluded that 30% is the optimum concentration of ethyl alcohol in hydroalcoholic systems when higher viscosity of the gel was required and 30% also for isopropyl alcohol when strong mucoadhesives are required for Cp 940 gel formulations.

Further to this, the document Tzaneva et al., J. Pharm. Sci. & Res. Vol. 9(8), 2017, 1383-1387 discloses modifications of chitosan with improved solubility for new cosmetic gel applications. It was found that chitosan can be modified chemically so as to be useful for the preparation of cosmetic gel formulations intended for skin formulations which impart a feeling of smoothness to the skin and protect it from adverse environmental conditions and dehydration. Gregolin et al., Journal of Dispersion Science and Technology, 31:820-825, 2010 provides a study on the rheological characteristics of gels with a focus on the use as a cosmetic base. The gels were prepared with sodium carboxymethyl cellulose 3% and 5%, with Carbopol 940 and with Carbopol Ultrez. It was found that a gel with 3% of sodium carboxymethyl cellulose presented the most appropriated behavior and is suitable as a cosmetic base. This means that for the efficiency and quality and consumer acceptance of cosmetic products, the rheological characteristics are a precious tool. The prior art also shows that there are wide variety of gel formulations for cosmetic use and the suitability for a specific application is not just an obvious variation of the tools and knowledge known from the prior art.

To adapt to a specific purpose, such as the present use of a fragrance gel in a sachet, the ingredients must be specifically chosen and balanced in their ratios with each other. To be usable in the sachets of the present invention, the product must have specific flow features, i.e. it must not flow out of the sachet easily but only upon pressing by the consumer with his fingers so as to press out the whole amount of the gel from the sachet. Unlike the perfume compositions of the prior art the present gel composition is not too liquid-like to be used only in a bottle, but it does also not linger on the skin like low viscosity gels. The composition is smooth on the skin and quickly absorbed.

The present inventors have now found out that when a basic composition is prepared, which comprises a gelling agent selected from acrylates/$C_{10}$-$C_{30}$ alkyl-acrylate crosspolymers, a cosmetically acceptable alcohol, water, stabilizer and a solubilizer in defined ratios then this basic composition is suitable to be combined with a variety of fragrances having defined properties, and have thus obtained a gel composition suitable for use in a sachet.

It has surprisingly been found that a perfume gel composition having the above favourable properties can be prepared by a composition having the above basic components, wherein the amount of alcohol (ethanol, isopropanol or mixtures thereof) is above 60% w/w and the fragrance composition is a composition of aromatic oils having defined physical properties and is present in an amount of 0.8 to 9.0% by weight and wherein the ratio of the fragrance composition:gelling agent:alcohol is from 1:0.06:6 to 1:0.16:12.5.

The percentage of alcohol at or above 60% w/w while maintaining the viscosity, is a unique feature of the composition, and obtained due to exclusive combination of the ingredients with the composition of the perfume, which is added in relativity high amount, compared with common formulation of alcoholic gel for sanitations exist in the market.

Contrary to the corresponding compositions of the prior art such as hand sanitizers or gel preparations that contain up to 50% alcohol, the composition of the present invention will not be liquidized due to the high alcohol concentration and can thus be packed into a sachet instead of bottles.

The formulation of the gel into which the fragrance or perfume is contained is characterized by a unique viscosity. Said viscosity is obtained by a matrix structure of an alcohol-aqueous phase that enables the cross polymer to be solubly dispersed in said spreading phase. Acrylates/$C_{10}$-$C_{30}$ alkyl-acrylate cross-polymers also contain some other monomers that are hydrophobic. This means that the molecule is partly hydrophobic and partly hydrophilic so that it not only works as a thickener but also as an emulsion stabilizer. It is very common in gel-type formulations that also an oily phase is contained. The perfume as such is hydrophobic and is solubilized and dispersed as micro oily drops protected by the PEG 40 hydrogenated castor oil and dispersed in the aqueous alcoholic phase of the preparation.

The perfume composition comprises a fragrance composition which has a liquid bulk specific gravity 20/20° C. of 0.97 to 1.08, a refractive index at 20° C. of 1.45 to 1.53 and a flash point of 100° C. to 1000° C. Any fragrance composition having said properties may be incorporated into the perfume composition of the invention.

The composition of the fragrance to be added to the perfume composition of the invention includes (preferably) Florol™, Cedror™, limonene, citral and *Eucalyptus*. The specific physical characteristic of the aromatic oils and compound in combination with the alcohol and cross-polymer create unique balance at enable the stable rheological features of the preparation in the sachet pack of alcoholic gel perfume that is pioneer in the fragrance market.

The composition may contain any type of fragrance having the above defined physical properties that is commonly used in perfumery products for human consumption. Specific examples thereof are:

| Substance | CAS | % In the fragrance compound or Raw material | mg/kg |
|---|---|---|---|
| 5-Acetyl-1,1,2,3,3,6-hexamethyl indan (Phantolide) | 15323-35-0 | | |
| Allyl heptane carbonate | 73157-43-4 | | |
| Amyl cyclopentenone (2-Pentyl-2-cyclopenten-1-one) | 25564-22-1 | | |
| Angelica root oil | 8015-64-3 | | |
| cis-and trans-Asarone ((E)-and(Z)-2,4,5-Trimethoxypropen-1-yl benzene) | Listed | | |
| Bergamot oil expressed | 8007-75-8 | | |
| Bitter Orange Peel Oil Expressed | 68916-04-1 | | |
| BMHCA (p-t-Butyl-alpha-methylhydrocinnamic aldehyde) | 80-54-6 | | |
| p-tert-Butyl-dihydrocinnamaldehyde (Bourgeonal) | 18127-01-0 | | |
| Cinnamic alcohol | 104-54-1 | | |
| Cinnamic aldehyde | 104-55-2 | | |
| Cinnamyl Nitrile | 1885-38-7 | | |
| Cumin oil | 8014-13-9 | | |
| Eugenol | 97-53-0 | | |
| Cyclamen alcohol (3-(4-Isopropylphenyl)-2-methylpropanol) | 4756-19-8 | | |
| Grapefruit oil expressed | 8016-20-4 | | |
| Trans-2-Hexenal | 6728-26-3 | | |
| alpha-Hexylidene cyclopentanone | 17373-89-6 | | |
| HMPCC (3 and 4-(4-Hydroxy-4-methylpentyl)-3- | 31906-04-4 | | |

| Substance | CAS | % In the fragrance compound or Raw material | mg/kg |
|---|---|---|---|
| cyclohexene-1-carboxaldehyde) | 51414-25-6 | | |
| Hydroxycitronellal (Laurine, Hydronal, Phixia, Laurinal) | 107-75-5 | | |
| Isocyclogeraniol (2,4,6-Trimethyl-3-cyclohexene-1-methanol) | 68527-77-5 | | |
| Isoeugenol | 97-54-1 | | |
| Lemon oil cold pressed | 8008-56-8 | | |
| Lime oil expressed | 8008-26-2 | | |
| Menthadienyl formate (Isobergamate) | 68683-20-5 | | |
| Methoxy dicylopentadiene carboxaldehyde (Scentenal) | 86803-90-9 | | |
| 2-Methoxy-4-methylphenol (Creosol) | 93-51-6 | | |
| Methyl heptadienone (6-Methyl-3,5-heptadienone) | 1604-28-0 | | |
| Methyl heptine carbonate (MHC, Folione) | 111-12-6 | | |
| Methyl N-methyl anthranilate (Dimethyl anthranilate) | 85-91-6 | 0.0153 | 153 |
| Methyl octine carbonate (MOC) | 111-80-8 | | |
| 3-Methyl-2(3)-nonenenitrile (Citgrenile) | 53153-66-5 | | |
| Methyleugenol | 93-15-2 | 0.0013 | 13 |
| p-Methylhydrocinnamic aldehyde | 5406-12-2 | | |
| Oak moss extracts (including solvent of codistillation) | 90028-68-5 | | |
| 1-Octen-3-yl acetate (Amyl vinyl carbinyl acetate) | 2442-10-6 | | |
| Opoponax | 9000-78-6 | | |
| Perilla aldehyde | 2111-75-3 | | |
| Peru balsam | 8007-00-9 | | |
| Petitgrain Mandarin Oil | 8014-17-3 | | |
| Propylidene phthalide | 17369-59-4 | | |
| Rue oil | 8014-29-7 | | |
| Safrol Natural | 94-59-7 | | |
| Styrax | listed | | |
| Tagetes oil and absolute | listed | | |
| Tree moss extracts (including cedarmoss and solvent of codistillation) | 90028-67-4 | | |
| 2,6,6-Trimethyleyclohexa-1,3-dienyl methanal (Safranal) | 116-26-7 | | |
| l-(Trimethylcyclohexenyl/cyclohexadienyl)-2-buten-1-ones (Rose ketones) | listed | | |
| Verbena absolute | 8024-12-2 | | |
| | 85116-63-8 | | |
| Benzyl cyanide natural | 140-29-4 | | |
| Methyl beta naphtyl ketone | 93-08-3 | | |
| Citral | 5392-40-5 | 0.0191 | 191 |
| Farnesol | 4602-84-0 | | |
| Phenylacetaldehyde | 122-78-1 | | |
| Tea extracts | 84650-60-2 | | |
| Acetaldehyde | 75-07-0 | | |
| Furfural | 98-01-1 | | |
| Bergapten | 484-20-8 | | |
| Benzyl alcohol | 100-51-6 | | |
| Cetone muse | 81-14-1 | 0.0769 | 769 |
| Thymol (added as such) | 89-83-8 | 0.0003 | 3 |
| Xylene musc | 81-15-2 | | |
| 2-Phenoxyethanol | 122-99-6 | | |
| Benzoic acid (added as such) | 65-85-0 | | |
| alpha-Amyl cinnamic alcohol | 101-85-9 | | |
| alpha-Amyl cinnamic aldehyde | 122-40-7 | | |
| alpha-Hexyl cinnamic aldehyde | 101-86-0 | | |
| alpha-Methyl cinnamic aldehyde | 101-39-3 | | |
| Anisyl alcohol | 105-13-5 | | |
| Benzyl benzoate | 120-51-4 | 0.0001 | 1 |
| Benzyl cinnamate | 103-41-3 | | |
| Benzyl salicylate | 118-58-1 | 0.0001 | 1 |
| Citronellol | listed | 0.1614 | 1614 |
| Geraniol | 106-24-1 | 01472 | 1472 |
| Hexyl salicylate | 6259-76-3 | 0.0769 | 769 |
| Isocyclocitral | listed | | |
| Methyl ionone mixed isomers | listed | 0.2307 | 2307 |
| Coumarin | 91-64-5 | | |
| 2,2-Dimethyl-3-(3-methylphenyl)propanol (Majantol) | 103694-68-4 | | |
| OTNE(1-(1,2,3,4,5,6,7,8-Octahydro-2,3,8,8-tetramethyl-2-naphthalenyl)ethanone) | 54464-57-2 | 10.7692 | 107692 |

-continued

| Substance | CAS | % In the fragrance compound or Raw material | mg/kg |
|---|---|---|---|
| 2-Ethoxy-4-methylphenol | 2563-07-7 | | |
| Carvone | 99-49-0 | 0.001 | 10 |
| | 2244-16-8 | | |
| | 6485-40-1 | | |
| Ylang Ylang (various extracts) | 8006-81-3 | | |
| | 68606-83-7 | | |
| | 83863-30-3 | | |
| Jasmine absolute (Grandiflorum) | 8022-96-6 | | |
| | 8024-43-9 | | |
| | 90045-94-6 | | |
| | 84776-64-7 | | |
| Jasmine absolute (Sambac) | 91770-14-8 | | |
| 7-Methoxycoumarin natural | 531-59-9 | | |
| AHTN (Tonalid) | 21145-77-7 | | |
| Benzo[a]pyrene (ppm) | 50-32-8 | | |
| Benzanthracene (ppm) | 56-55-3 | | |
| 1-(5,5-dimethyl-1-cyclohexen-1-yl)-pent-4-en-1-one | 56973-85-4 | | |
| 2-Phenylpropionaldehyde (Hydratropic aldehyde) | 93-53-8 | | |
| 4-Methoxy-alpha-methylbenzenepropanal (Canthoxal) | 5462-06-6 | | |
| Allyl phenoxyacetate | 7493-74-5 | | |
| Benzaldehyde | 100-52-7 | | |
| Cinnamic aldehyde dimethyl acetal | 4364-06-1 | | |
| Dibenzyl ether | 103-50-4 | | |
| Melissa oil | 8014-71-9 | | |
| Isobutyl-methyl hydro cinnamic aldehyde(Sylvial/Suzaral/Rhodial) | 6658-48-6 | 0.0242 | 242 |
| Acetylated Vetiver oil | 62563-80-8 | | |
| | 117-98-6 | | |
| | 68917-34-0 | | |
| | 84082-84-8 | | |
| | 73246-97-6 | | |
| 1,2,3,4-Tetrahydro-4-methylquinoleine | 19343-78-3 | | |
| Isobutyl N-methyl anthranilate | 65505-24-0 | | |
| p-Methyltetrahydroquinoline | 91-61-2 | | |
| Estragole | 140-67-0 | | |
| Dimethylcyclohex-3-ene-1-carbaldehyde (mixed isomers) | 68737-61-1 | 0.0307 | 307 |
| | 68039-49-6 | | |
| | 68039-48-5 | | |
| | 27939-60-2 | | |
| | 67801-65-4 | | |
| | 36635-35-5 | | |
| | 68084-52-6 | | |
| | 35145-02-9 | | |
| alpha-Methyl-1,3-benzodioxole-5-propionaldehyde (MMDHCA) | 1205-17-0 | 0.6153 | 6153 |
| 3-Phenylbutanal | 16251-77-7 | | |
| a-Butylcinnamaldehyde | 7492-44-6 | | |
| 2-Heptylidene cyclopentan-1-one | 39189-74-7 | | |
| o-Methyoxycinnamaldehyde | 1504-74-1 | | |
| p-Methoxybenzaldehyde | 123-11-5 | | |
| o,m,p-Tolualdehydes and their mixtures | 529-20-4 | | |
| | 620-23-5 | | |
| | 104-87-0 | | |
| | 1334-78-7 | | |
| Dihydrocoumarin | 119-84-6 | | |
| 6,7-Dihydro-1,1,2,3,3-pentamethyl-4(5H)-indanone (DPMI) | 33704-61-9 | 0.1538 | 1538 |
| 3-(m-tert-Butylphenyl)-2-methylpropionaldehyde (m-BMHCA) | 62518-65-4 | | |
| Acetic acid, anhydride, reaction products with 1,5,10-trimethyl-1,5,9-cyclododecatriene | 144020-22-4 | | |
| | 28371-99-5 | | |
| Ethoxydiglycol | 111-90-0 | | |

The ratio of the fragrance composition:gelling agent: alcohol is from 1:0.06:6 to 1:0.16:12.5 including subranges.

Moreover, the composition may also contain trace quantities (less than 0.001% w/w) of the following ingredients: linalool, limonene, ethylhexyl methoxycinnamate, benzyl salicylate, hexyl cinnamal, hydroxycitronellal, butyl methoxydibenzoylmethane, ethylhexyl salicylate, alpha-Isomethyl ionone, citronellol, coumarin, BHT, geraniol, eugenol, citral, benzyl benzoate, benzyl alcohol, farnesol, tocopherol.

The perfume composition of the present invention is a gel having a viscosity of 17,500 to 24,200 cps, preferably from 19,000 to 23,000 cps and most preferably from 19,000 to 22,000 cps at ambient temperature including all ranges subsumed therein.

The components of the perfume composition of the present invention are limited only to the extent that they may be combined to make a gel having the above described viscosities and that they do not degrade the structural properties of the sachet. Typical other components that may be included in the perfume gel composition are herbal extracts from plants, moisturizing agents to protect the skin while using an alcoholic gel perfume, aromatic oils such as lavender and orange blossom aroma oil.

The composition comprises 0.2 to 2.0% by weight of a gelling agent which is selected from acrylates/$C_{10}$-$C_{30}$ alkyl-acrylate cross polymers. This is a hydrophobically modified crosslinked acrylate copolymer and is designed to efficiently impart thickening, stabilizing and suspending properties to the perfume gel composition. Said polymer is known in the art and is commercially available.

The Acrylates/$C_{10}$-30 Alkyl Acrylate Crosspolymer is a proprietary copolymer of $C_{10\text{-}30}$ alkyl acrylate and one or more monomers of acrylic acid, methacrylic acid or one of their simple esters crosslinked with an allyl ether of sucrose or an allyl ether of Penta [1]. This gelling agent ingredient might be any branded name of trade name synonym to Carbopol® Ultras 20 Polymer[2].

For example, 9 branded names of this polymer, manufactured by Lubrizol[3]:

9 Products Found

| Name | Technology | Supplier | Docs & Support |
| --- | --- | --- | --- |
| Carbopol ® 1342 polymer | Cross linked Acrylics | Lubrizol | |
| Carbopol ® 1382 polymer | Cross linked Acrylics | Lubrizol | |
| Carbopol ® ETO 2020 golymer | Cross linked Acrylles | Lubrizol | |
| Carbopol ® SC-200 polymer | Cross linker Acrylics | Lubrizol | |
| Carbopol ® Ultrez 20 polymer | Cross linked Acrylics | Lubrizol | |
| Carbopol ® Ultrez 21 polymer | Cross linked Acrylics | Lubrizol | |
| Pemolen ™ EZ-4U polymeric emulsifier | Thickeners Stabilizers Emulsifiers | Lubrizol | |
| Pemulen ™ TR-1 polymer | Synthetic Polymers Synthetic Blends Emulsifiers O W Oil in Water | Lubrizol | |
| Pemulen ™ TR-2 polymer | Cross linked Acrylics Enulsifiers O W Oil in Water | Lubrizol | |

1: productingredients.com/ingredient/info/acrylatesc 10-30-alkyl-acrylate-crosspolymer
2: ulprospector.com/en/na/PersonalCare/Detail/76/28581/Carbopol-Ultrez-20-Polymer
3: cosmetics.specialchem.com/inci/acrylates-c10-30-alkyl-acrylate-crosspolymer/s-lubrizol 1: productingredients.com/ingredient/info/acrylatesc10-30-alkyl-acrylate-crosspolymer 2: ulprospector.com/en/na/PersonalCare/Detail/76/28581/Carbopol-Ultrez-20-Polymer 3: cosmetics.specialchem.com/inci/acrylates-c10-30-alkyl-acrylate-crosspolymer/s-lubrizol In the following, exemplary and preferred embodiments of crosslinked alkyl acrylates as used in cosmetic formulations are given. These crosslinked polymers consist of co-monomers of at least one of: acrylic acid, sodium acrylate, methacrylic acid, or alkyl acrylate that share chemical properties, including a general lack of chemical reactivity. The ingredients included in this group are:

Acrylates/C10-30 Alkyl Acrylate Crosspolymer
Acrylates/C12-13 Alkyl Methacrylates/Methoxyethyl Acrylate Crosspolymer
Acrylates Crosspolymer
Acrylates/Ethylhexyl Acrylate Crosspolymer
Acrylates/Ethylhexyl Acrylate/Glycidyl Methacrylate Crosspolymer
Acrylates/PEG-4 Dimethacrylate Crosspolymer
Acrylates/Steareth-20 Methacrylate Crosspolymer
Acrylates/Vinyl Isodecanoate Crosspolymer
Acrylates/Vinyl Neodecanoate Crosspolymer
Allyl Methacrylate/Glycol Dimethacrylate Crosspolymer
Allyl Methacrylates Crosspolymer
Butyl Acrylate/Glycol Dimethacrylate Crosspolymer
C8-22 Alkyl Acrylates/Methacrylic Acid Crosspolymer
Glycol Dimethacrylate/Vinyl Alcohol Crosspolymer
Lauryl Methacrylate/Glycol Dimethacrylate Crosspolymer
Lauryl Methacrylate/Sodium Methacrylate Crosspolymer
Methacrylic Acid/PEG-6 Methacrylate/PEG-6 Dimethacrylate Crosspolymer
PEG/PPG-5/2 Methacrylate/Methacrylic Acid Crosspolymer
Potassium Acrylates/$C_{10\text{-}30}$ Alkyl Acrylate Crosspolymer
Sodium Acrylates Crosspolymer-2
Sodium Acrylates/C10-30 Alkyl Acrylate Crosspolymer
Sodium Acrylates/Vinyl Isodecanoate Crosspolymer
Stearyl/Lauryl Methacrylate Crosspolymer Crosslinked alkyl acrylates are crosslinked polymers in which the co-monomers consist of at least one of the following: acrylic acid, sodium acrylate, methacrylic acid, or alkyl acrylate. Whereas polymers consisting purely of acrylic acid are often referred to as "carbomers," copolymers comprised of mixtures of acrylic acid and alkyl acrylate monomers may sometimes be referred to as "alkyl carbomers."

Gelling agents to be used in combination with the above acrylates/$C_{10}$-$C_{30}$ alkyl-acrylate cross polymers are Polyacrylate Crosspolymer-6, or Hydroxyethyl Acrylate/Sodium Acryloyldimethyl Taurate Copolymer or Polyacrylamide (and) C13-14 Isoparaffin (and) Laureth-7 or Acrylates Copolymer or carbomer.

A cosmetically acceptable alcohol is used as a solvent in an amount of 60 to 75%, preferably 65 to 70%, and more preferably 60 to 68% w/w including all subranges. The alcohol is preferably selected from ethanol, isopropanol and mixtures thereof. Mixtures of ethanol and isopropanol are preferably mixtures having 50% ethanol and 50% isopropanol, mixtures having 30% ethanol and 70% isopropanol or mixtures having 30% isopropanol and 70% ethanol.

Moreover, the composition comprises 0.5 to 1.5% by weight of a stabilizer. Basically any stabilizer which is known in the art as cosmetically acceptable may be used. Preferably the stabilizer is selected from lauryl lactate, myrisic lactate and cetyl lactate or a mixture thereof, or from ethyl lactate, butyl lactate, hexyl lactate, octyl lactate, decyl lactate and ocatadecyl lactate or mixtures thereof. Most preferably the stabilizer is selected from lauryl lactate, myrisic lactate and cetyl lactate or a mixture thereof.

Moreover, the composition comprises 0.5 to 2.4% by weight of a solubilizer. Basically, any solubilizer that is cosmetically acceptable can be used. Preferably the solubilizer is selected from PEG 40 hydrogenated castor oil, or Polyglyceryl-10 Laurate or Caprylyl/Capryl Wheat Bran/Straw Glycosides, Aqua, Fusel Wheat Bran/Straw Glycosides, Polyglyceryl-5 Oleate, Sodium Cocoyl Glutamate, Glyceryl Caprylate or Polyglyceryl-10 Caprylate.

Additionally, the gel composition may include other materials including, but not limited to, surfactants, fillers, further solvents, fragrance stabilizers, disinfectants etc.

The perfume composition of the invention is added up to 100% by weight with water, i.e. the difference from the total of the above other ingredients to 100% is added with water.

It is, however, preferred that the gel composition of the present invention contains a minimum of ingredients and does not contain any harmful substances.

The gel composition of the present invention is preferably a transparent gel, but it may also contain natural coloring agents such as green tea extract, algae extract etc.

The perfume composition is a gel composition within the scope of present claim 1 as regards the ingredients and their ratios. Exemplary formulations may be formulations which contain restricted amounts of the general ingredients (as the one specified above) and/or compositions which comprise a specific combination of ingredients in specific percentages.

The perfume/gel composition of the invention is contained in a unit dose sachet. Usually, the packaging form of a sachet is used in the cosmetic industry as a means for sample distribution, but according to the present invention, the packaging form of a sachet is the product meant to provide the full experience. It is not a travel-size product but is intended for everyday use.

Said sachet may be any type of standard industry laminated packet structure such as a polyethylene film or any other suitable material including 100% biodegradable materials such as naturally occurring fibres such as bamboo, hemp roots or gum-Arabic fibres.

Figure 1:
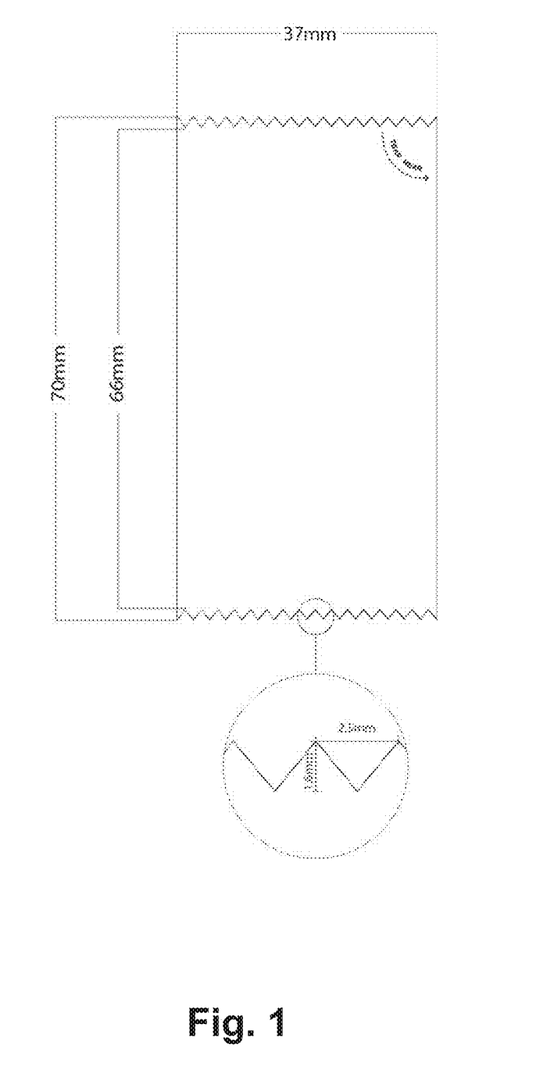
FIG. 1 shows an example for the dimensioning and structure of the unit dose sachet of the invention.

The sachet preferably has a convenient size for everyday use, such as ketchup or mayonnaise sachet. FIG. 1 shows an exemplary design of a sachet to be used according to the present invention. The sachet, however, may also have a fancy form such as a sausage form, a French fries form, a chips form, a fancy bottle form. The sachet may be in various colors.

Figure 2:
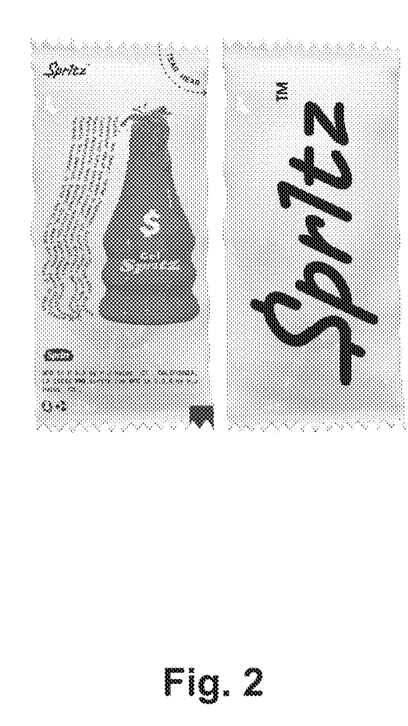
FIG. 2 shows an exemplary package of the unit dose sachet of the present invention.

The logo print of the product (Spr1tz) is applied to the surface of the sachet in a manner known to a person skilled in the art. The backside of the sachet specifies the ingredients as required by legal prerequisites. The sachet contains a tear-open corner. FIG. 2 shows both sides of an exemplary sachet according to the present invention.

Figure 3:
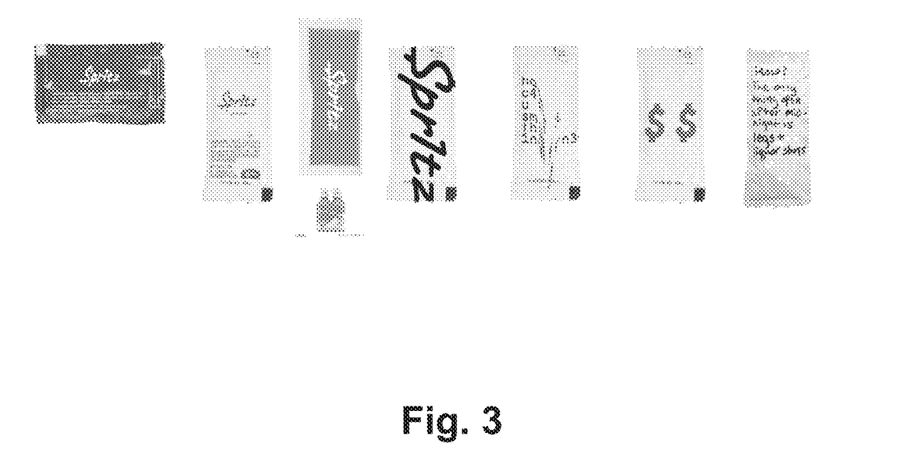
FIG. 3 shows variations in the design of the unit dose sachet of the invention.

FIG. 3 shows further examples of design packages.

The perfume/fragrance gel according to the present invention is prepared in a manner known in the art, usually by conventional mixing, dispersing in cold process combined with heating some of the ingredients in order to melt and combine them before adding to the dispensing phase. Specific temperature and stirring conditions not harmful to any of the ingredients and the fragrance compound are to be applied.

The unit dose sachets may be sold in packages comprising a monthly supply of 30 sachets or in larger packages such as carton or other material that is sustainable and environmentally friendly.

The unique combination of ingredients and fragrance extracts combined with a sachet form as the packaging form enables the preservation of the characteristics of the perfume product for a long shelf live without the use of harmful preservatives or other additives. The unique composition of the fragrance gel in a specific packaging form is to provide the customer with a unique and new experience in the field of perfumery. Hence, the invention also relates to the cosmetic use of the above unit dose sachet for creating a scented atmosphere surrounding the human body by rubbing the composition into the skin. The composition may repeatedly be rubbed into the skin to refresh the unique experience of personal perfuming.

The invention will now be described further with reference to the following examples.

The exemplary formulations of the following examples provide gel perfume compositions to be conveniently used in a sachet.

In the examples, the following methods were used to determine the physical properties of the compounds:

Refractive Index

The refractive index was measured at 20° C. and is indicated as the D line of sodium (doublet at 589.0 nm and 589.6 nm). The refractive index is preferably measured by an Abbé refractometer.

Viscosity

The viscosity is measured with a Brookfield type viscometer at 23° C. according to the instructions of the manufacturer.

Specific Gravity

The specific gravity is measured by a pycnometer at 20° C.

Example 1: Exemplary Formulation of a Unit Dose Sachet

Formulation A

| % (W/W) | Commercial Name | INCI Name |
|---|---|---|
| Sfq 100 | DEIONISED WATER | Aqua |
| 0.5 | CARBOPOL ETD2020 | Acrylate/C10-30 Alkyl acrylate Crosspolymer |
| 67.0 | ISOPROPYL ALCOOL(IPA) 96° | Isopropylalcohol |
| QS pH 6.5 | AMINO METHYL PROPANOL | Aminomethylpropanol |
| 7-8 | FRAGRANCE | Fragrance (Parfum) |

Formulation B

| % (W/W) | Commercial Name | INCI Name |
|---|---|---|
| Sfq 100 | DEIONISED WATER | Aqua |
| 0.5 | CARBOPOL ETD2020 | Acrylate/C10-30 Alkyl acrylate Crosspolymer |
| 67.0 | ETHL ALCOOL 96° | Ethyl Alcohol |
| QS pH 6.5 | AMINO METHYL PROPANOL | Aminomethylpropanol |
| 8 | FRAGRANCE | Fragrance (Parfum) |

Viscosity range 19,000 to 22,000 cps.

In the above formulations the amount of fragrance can be varied depending on the intended intensity of the product. The amount of water is to be adapted to achieve 100%.

The ingredients may be formulated to a gel according to any method of formulating a gel composition known in the art.

The ingredients are preferably formulated to a gel according to Example 10. Depending on the formulation method the viscosity range is 19,000 to 22,000 cps.

Example 2: Exemplary Formulation of a Unit Dose Sachet

| Ingredient | % (W/W) |
| --- | --- |
| WATER | To 100.00 |
| ULTRATHIX 21 (ACRYLATES/C10-C30 ALKYL ACRYLATE CROSSPOLYMER) | 0.4 |
| ISOPROPYL ALCOOL(IPA) 96° | 67 |
| PERFUME | 7-9 |
| PEG 40 HYDROGENATED COSTER OIL | 1-2 |
| CERAPHYL 31 (LAURYL LACTATE (AND) MYRISTYL LACTATE (AND) CETYL LACTATE) | 1.5 |

The ingredients may be formulated to a gel according to any method of formulating a gel composition known in the art.

The ingredients are preferably formulated to a gel according to Example 10.

Depending on the formulation method the viscosity range is 19,000 to 22,000 cps.

Example 3: Exemplary Formulation of a Unit Dose Sachet

Formulation A

| Ingredient | % (W/W) |
| --- | --- |
| WATER | To 100.00 |
| ULTRATHIX 21 (ACRYLATES/C10-C30 ALKYL ACRYLATE CROSSPOLYMER) | 0.4 |
| ETHYL ALCOHOL | 70 |
| PERFUME | 8-9 |
| PEG 40 HYDROGENATED COSTER OIL | 0.4-2.4 |
| CERAPHYL 31 (LAURYL LACTATE (AND) MYRISTYL LACTATE (AND) CETYL LACTATE) | 1 |

Formulation B

| Ingredient | % (W/W) |
| --- | --- |
| WATER | To 100.00 |
| ULTRATHIX 21 (ACRYLATES/C10-C30 ALKYL ACRYLATE CROSSPOLYMER) | 0.4 |
| ISOPROPYL ALCOOL(IPA) 96° | 70 |
| PERFUME | 8 |
| PEG 40 HYDROGENATED COSTER OIL | 2.0 |
| CERAPHYL 31 (LAURYL LACTATE (AND) MYRISTYL LACTATE (AND) CETYL LACTATE) | 1 |

In the above formulation A the amounts of ingredients can be varied within the indicated ranges. The total compounds have to add up to 100%.

The formulation B is a preferred formulation of formulation A.

The ingredients may be formulated to a gel according to any method of formulating a gel composition known in the art.

The ingredients are preferably formulated to a gel according to Example 10. Depending on the formulation method the viscosity range is 19,000 to 22,000 cps.

Example 4: Exemplary Formulation of a Unit Dose Sachet

| % (W/W) | Commercial Name | INCI Name |
| --- | --- | --- |
| Sq. 100 | DEIONISED WATER | Aqua |
| 0.3 | CARBOPOL ETD2020 | Acrylate/C10-30 Alkyl acrylate |
| 0.3 | SEPIMAX ZEN ™ | Cross-polymer Polyacrylate Crosspolymer-6 |
| 67.0 | ETHYL ALCOHOL 96° | Ethyl Alcohol |
| QS pH 6.5 | AMINO METHYL PROPANOL | Aminomethylpropanol |
| 7-9 | FRAGRANCE FORBIDDEN GARDEN G120 18129 | Fragrance (Parfum) |

The amount of fragrance can be varied depending on the intended intensity of the product. The amount of water is to be adapted to achieve 100%.

The ingredients may be formulated to a gel according to any method of formulating a gel composition known in the art.

The ingredients are preferably formulated to a gel according to Example 10.

Depending on the formulation method the viscosity range is 19,000 to 22,000 cps.

Example 5: Exemplary Formulation of a Unit Dose Sachet

| Ingredient | % (W/W) |
| --- | --- |
| WATER | Ad 100.00 |
| SEPINOV ™ EMT 10 (Hydroxyethyl Acrylate/Sodium Acryloyldimethyl Taurate Copolymer) | 0.8 |
| ISOPROPYL ALCOOL(IPA) 96° | 62 |
| PERFUME FORBIDDEN GARDEN G120 18129 | 8-9 |
| CERAPHYL 31 (LAURYL LACTATE (AND) MYRISTYL LACTATE (AND) CETYL LACTATE) | 1.5 |

The ingredients may be formulated to a gel according to any method of formulating a gel composition known in the art.

The ingredients are preferably formulated to a gel according to Example 10. Depending on the formulation method the viscosity range is 19,000 to 22,000 cps.

Example 6: Exemplary Formulation of a Unit Dose Sachet

Formulation A

| Ingredient | % (W/W) |
| --- | --- |
| WATER | Ad 100.00 |
| ULTRATHIX 21(ACRYLATES/C10-C30 ALKYL ACRYLATE CROSSPOLYMER) | 0.4 |
| ETHYL ALCOHOL | 60 |
| PERFUME FORBIDDEN GARDEN G120 18129 | 8-9 |
| PEG 40 HYDROGENATED COSTER OIL | 2.4 |
| CERAPHYL 31 (LAURYL LACTATE (AND) MYRISTYL LACTATE (AND) CETYL LACTATE) | 1 |

Formulation B

| Ingredient | % (W/W) |
|---|---|
| WATER | Ad 100.00 |
| ULTRATHIX 21(ACRYLATES/C10-C30 ALKYL ACRYLATE CROSSPOLYMER) | 0.4 |
| ISOPROPYL ALCOOL(IPA) 96° | 60 |
| PERFUME FORBIDDEN GARDEN G120 18129 | 9 |
| PEG 40 HYDROGENATED COSTER OIL | 2.4 |
| CERAPHYL 31 (LAURYL LACTATE (AND) MYRISTYL LACTATE (AND) CETYL LACTATE) | 1 |

The ingredients may be formulated to a gel according to any method of formulating a gel composition known in the art.

The ingredients are preferably formulated to a gel according to Example 10.

Depending on the formulation method the viscosity range is 19,000 to 22,000 cps.

Example 7: Exemplary Formulation of a Unit Dose Sachet

| % (W/W) | Commercial Name | INCI Name |
|---|---|---|
| Sfq 100 | DEIONISED WATER | Aqua |
| 0.5 | CARBOPOL ETD2020 | Acrylate/C 10-30 Alkyl acrylate Crosspolymer |
| 66.0 | ETHYL ALCOOL 96° | Ethyl Alcohol |
| QS pH 6.5 | AMINO METHYL PROPANOL | Aminomethylpropanol |
| 6.5 | FRAGRANCE | Fragrance (Parfum) |

*FRAGRANCE FORBIDDEN GARDEN G120 18129

The ingredients may be formulated to a gel according to any method of formulating a gel composition known in the art. The ingredients are preferably formulated to a gel according to Example 10. Depending on the formulation method the viscosity range is 19,000 to 22,000 cps.

Example 8: Exemplary Formulation of a Unit Dose Sachet

| COMPONENTS | INCI DECLARATION | % |
|---|---|---|
| Water | Aqua | Up to 100 |
| Alcohol (96°) | Ethanol | 65.0 |
| Fragrance | Fragrance (parfum) | 9 |
| Isopropanol | Isopropanol | 15.0 |
| Jojoba Aqua Sol-120W | Jojoba Wax PEG-120 esters | 0.1 |
| Synthalen L | Carbomer | 0.6 |
| AMP-Utra PC 2000 | Aminomethyl Propanol | a.n. |

The ingredients may be formulated to a gel according to any method of formulating a gel composition known in the art.

The ingredients are preferably formulated to a gel according to Example 10.

Depending on the formulation method the viscosity range is 19,000 to 22,000 cps.

Example 9: Exemplary Formulation of a Unit Dose Sachet

| Material Name | INCI | % (W/W) |
|---|---|---|
| DEMINERALIZED WATER | AQUA | To 100.00 |
| EDTA | EDTA | 0.05 |
| GENENCARE ® OSMS BA | BETAINE | 2.00 |
| GLYCERINE | GLYCERIN | 2.00 |
| CARBOPOL ULTREZ 21 | ACRYLATES/C10-30 ALKYL ACRYLATE CROSSPOLYMER | 0.60 |
| ISOPROPYL ALCOOL(IPA) 96° | ALCOHOL | 60.00 |
| AMP ULTRA PC 2000 (5% WATER) | AMINOMETHYL PROPANOL, WATER | 0.14 (qsp pH = 6) |
| RESASSOL VH | PEG-40 HYDROGENATED CASTOR OIL, PPG-26 BUTETH-26 | 0.20 |
| FRAGRANCE | FRAGRANCE (PERFUME) | 8 |

The ingredients may be formulated to a gel according to any method of formulating a gel composition known in the art. The ingredients are preferably formulated to a gel according to Example 10. Depending on the formulation method the viscosity range is 19,000 to 22,000 cps.

Example 10: Preparation of a Unit Dose Sachet

The above formulations can be prepared by the following process:

The preparation process is usually a conventional process and comprises the following steps and sub steps:
 a. Preparation of the fragrance gel
 b. Filling fragrance gel into the sachet
  a) Step: Preparation of the fragrance gel
  1. Dispersing in the aqua phase the gelling agent by sheer force of homogenizer, adding to the dispersion
  2. In separate vessels heating the solubilizer and stabilizers until fully melted and adding the perfume to the melted mass.
  3. Mixing the alcohol with the melted mass and adding the mixture to the Aqua phase that contain the gelling agent. Continue missing the preparation with low sheer forces until homogenous mixture is achieve.
   After mixture is homogenous and stable, verify that PH is between 4.0-5.5 and desired viscosity gel is formed.
  b) Step: Filling fragrance gel into the sachet
   Filling the gel fragrance mixture into a dedicate sachet's filling machine reservoir and performing filling each sachet with weight amount of fragrance gel to create the fragrance gel final product.

What is claimed is:

1. A unit dose sachet comprising a perfume composition, wherein the perfume composition is a gel which comprises:
 i) 0.2 to 2.0% by weight of a gelling agent selected from acrylates/$C_{10}$-$C_{30}$ alkyl acrylate cross polymers;
 ii) 60.0 to 75.0% by weight of a cosmetically acceptable alcohol;
 iii) 0.8 to 9.0% by weight of a fragrance composition having a liquid bulk specific gravity 20/20° C. of 0.97 to 1.08, a refractive index at 20° C. of 1.45 to 1.53 and a flash point of 100° C. to 1000° C.;
 iv) 0.5 to 1.5% by weight of a stabilizer; and
 v) 0.5 to 2.4% by weight of a solubilizer, vi) water up to 100% by weight,
wherein the composition has a viscosity of 17,500 to 24,200 cps,
and wherein the ratio of fragrance composition:gelling agent:alcohol is from 1:0.06:6 to 1:0.16:12.5.

2. The unit dose sachet according to claim 1, wherein the perfume composition comprises one or more essential oils.

3. The unit dose sachet according to claim 1, wherein the perfume composition is a gel which comprises:
  i) 0.3 to 0.5% by weight of a gelling agent selected from acrylates/$C_{10}$-$C_{30}$ alkyl-acrylate cross polymers;
  ii) 60.0 to 68.0% by weight of a cosmetically acceptable alcohol;
  iii) 3.0 to 8.0% by weight of a fragrance composition having a liquid bulk specific gravity 20/20° C. of 0.97 to 1.08, a refractive index at 20° C. of 1.45 to 1.53 and a flash point of 100° C. to 1000° C.;
  iv) 1.0 to 1.4% by weight of a stabilizer; and
  v) 0.5 to 1.5% by weight of a solubilizer,
  vi) water up to 100% by weight,
  wherein the composition has a viscosity of 17,500 to 24,200 cps,
  and wherein the ratio of fragrance composition:gelling agent:alcohol is from 1:0.06:6 to 1:0.16:12.5.

4. The unit dose sachet according to claim 1, wherein the composition has a viscosity of 17,500 to 23,000.

5. The unit dose sachet according to claim 4, wherein the composition has a viscosity of 19,000 to 22,000 cps.

6. The unit dose sachet according to claim 1, wherein the cosmetically acceptable alcohol is selected from ethanol and isopropanol or mixtures thereof.

7. The unit dose sachet according to claim 1, wherein the sachet is made from a flexible material and has a size of not more than 4 cm×7 cm.

8. The unit dose sachet according to claim 1, wherein the sachet is hermetically sealed and can be opened for use by tearing one corner.

9. A package comprising a monthly supply of a unit dose sachet according to claim 1.

10. A method of using a unit dose sachet according to claim 1 for creating a scented atmosphere surrounding a human body comprising rubbing the perfume composition of claim 1 into the skin of a user.

* * * * *